United States Patent [19]
Pla et al.

[11] Patent Number: 5,793,210
[45] Date of Patent: Aug. 11, 1998

[54] LOW NOISE MRI SCANNER

[75] Inventors: Frederic Ghislain Pla; Robert Arvin Hedeen, both of Clifton Park, N.Y.; Robert James Dobberstein, New Berlin, Wis.; Thomas Gerard Ebben, Sullivan, Wis.; Scott Thomas Mansell, Waterford, Wis.; Kemakolam Michael Obasih, Brookfield, Wis.; Michael James Radziun, Waterford, Wis.; Peter Ping-Liang Sue, Florence, S.C.; William Alan Edelstein, Schenectady, N.Y.

[73] Assignee: General Electric Company, Schenectady, N.Y.

[21] Appl. No.: 696,077

[22] Filed: Aug. 13, 1996

[51] Int. Cl.⁶ .................................................. G01R 33/20
[52] U.S. Cl. ................................................... 324/318
[58] Field of Search ................................... 324/300, 307, 324/309, 318

[56] References Cited

U.S. PATENT DOCUMENTS

| | | | |
|---|---|---|---|
| 4,602,176 | 7/1986 | Baker . | |
| 4,680,545 | 7/1987 | Gray et al. | 324/307 |
| 5,084,676 | 1/1992 | Saho et al. | 324/318 |
| 5,179,338 | 1/1993 | Laskaris et al. . | |
| 5,225,782 | 7/1993 | Laskaris et al. . | |
| 5,278,502 | 1/1994 | Laskaris et al. . | |
| 5,489,848 | 2/1996 | Furukawa | 324/318 |

Primary Examiner—Sandra L. O'Shea
Assistant Examiner—Michael Eisenberg
Attorney, Agent, or Firm—Douglas E. Erickson; Marvin Snyder

[57] ABSTRACT

A magnetic-resonance-imaging (MRI) scanner subassembly. In one subassembly, a preferably annularly-cylindrical-shaped enclosure contains a first vacuum, and an MRI gradient coil assembly is located within the enclosure in the first vacuum. Preferably, an annularly-cylindrical housing is included which is coaxially aligned with the enclosure and contains a second vacuum which is higher than the first vacuum, and an MRI superconductive main coil is located within the housing in the second vacuum. In another subassembly, an MRI gradient coil assembly has a threshold excitation frequency, and an isolation mount assemblage supports the MRI gradient coil assembly.

5 Claims, 2 Drawing Sheets

LOW NOISE MRI SCANNER

BACKGROUND OF THE INVENTION

The present invention relates generally to a magnetic resonance imaging (MRI) scanner and more particularly to a low-noise subassembly for an MRI scanner.

MRI scanners, which are used in various fields such as medical diagnostics, typically use a computer to create images based on the operation of a magnet, a gradient coil assembly, and a radio-frequency coil(s). The magnet creates a uniform main magnetic field which makes atoms, such as hydrogen atoms, responsive to radio-frequency excitation. The gradient coil assembly imposes a pulsed, spatial-gradient magnetic field upon the main magnetic field to give each point in the imaging volume a spatial identity corresponding to its unique magnetic field. The radio-frequency coil creates an excitation frequency pulse which temporarily raises the energy level of the atoms, with the resulting energy decay being measured by the radio-frequency coil and used by the computer to create the image. Typically the radio-frequency coil, the gradient coil assembly, and the magnet are generally annularly-cylindrical shaped and are generally coaxially aligned, wherein the gradient coil assembly circumferentially surrounds the radio-frequency coil and wherein the magnet circumferentially surrounds the gradient coil assembly.

Magnets for MRI scanners include superconductive-coil magnets, resistive-coil magnets, and permanent magnets. Known superconductive magnets include liquid-helium cooled and cryocooler-cooled superconductive magnets. Typically, for a helium-cooled magnet, the superconductive coil assembly includes a superconductive main coil which is at least partially immersed in liquid helium contained in a helium dewar which is surrounded by a dual thermal shield which is surrounded by a vacuum enclosure. In a conventional cryocooler-cooled magnet, the superconductive main coil is surrounded by a thermal shield which is surrounded by a vacuum enclosure, and the cryocooler coldhead is externally mounted to the vacuum enclosure with the coldhead's first stage in thermal contact with the thermal shield and with the coldhead's second stage in thermal contact with the superconductive main coil. Nb-Ti superconductive coils typically operate at a temperature of generally 4 Kelvin, and Nb-Sn superconductive coils typically operate at a temperature of generally 10 Kelvin. The vacuum within the vacuum enclosure must be very low pressure to prevent unwanted heat transfer which can result in magnet "quenching" (i.e., loss of superconductivity). A typical vacuum is between generally $10^{-7}$ and generally $10^{-3}$ torr. It is noted that standard atmospheric pressure is defined to be 760 torr, that a vacuum is defined to have a pressure lower than that of atmospheric pressure.

Known superconductive magnet designs include closed magnets and open magnets. Closed magnets typically have a single, tubular-shaped superconductive coil assembly having a bore. The superconductive coil assembly includes several radially-aligned and longitudinally spaced-apart superconductive main coils each carrying a large, identical electric current in the same direction. Typically, the superconductive main coils are designed to create a magnetic field of high uniformity within a spherical imaging volume centered within the magnet's bore where the object to be imaged is placed.

Open magnets typically employ two spaced-apart superconductive coil assemblies with the space between the assemblies allowing for access by medical personnel for surgery or other medical procedures during MRI imaging. The patient may be positioned in that space or also in the bore of the toroidal-shaped coil assemblies. The open space helps the patient overcome feelings of claustrophobia that may be experienced in a closed magnet design.

The gradient coil assemblies of MRI scanners generate loud noises which many medical patients find objectionable. Active noise control techniques have been used to reduce gradient coil assembly noise including noise-canceling patient earphones. Known passive noise control techniques include locating the gradient coil assembly in the vacuum enclosure which contains the superconductive main coils.

It is known in the mechanical arts area to design and use isolation mounts so that vibrations from machinery supported by the isolation mounts are not transmitted to surrounding structure which supports the isolation mounts. Conventional isolation mounts include those of the elastomeric type and those of the spring type. Such isolation mounts are designed by the artisan so that the natural frequency of vibration of the mounts and the machinery is less than the dominant excitation frequency of the machinery divided by the square root of two to provide effective vibration isolation.

What is needed is a lower noise MRI scanner.

SUMMARY OF THE INVENTION

In a first embodiment, the magnetic-resonance-imaging (MRI) scanner subassembly of the invention includes an enclosure containing a first vacuum of between generally 1 and generally 250 torr and further includes an MRI gradient coil assembly which is disposed within the enclosure in the first vacuum and generally spaced apart from the enclosure.

In a second embodiment of the invention, the MRI scanner subassembly includes an enclosure, a housing, an MRI gradient coil assembly, and an MRI superconductive main coil. The enclosure is generally annularly-cylindrical-shaped, has a generally longitudinally-extending axis, and contains a first vacuum. The housing is generally annularly-cylindrical-shaped, is generally coaxially aligned with the axis, and contains a second vacuum which is a lower pressure vacuum than the first vacuum. The MRI gradient coil assembly is located within the enclosure in the first vacuum and is generally spaced apart from the enclosure. The MRI superconductive main coil is generally coaxially aligned with the axis and is located within the housing in the second vacuum.

In a third embodiment of the invention, the MRI scanner subassembly includes an MRI gradient coil assembly excited by a predetermined series of multi-frequency electrical pulses having an electrical power, wherein generally five percent of said electrical power of said series comes from frequencies no higher than a threshold excitation frequency and generally ninety-five percent of said electrical power of said series comes from frequencies higher than said threshold excitation frequency and further includes an isolation mount assemblage supporting the MRI gradient coil assembly. The isolation mount assemblage and the MRI gradient coil assembly together have a natural frequency of vibration which is less than the threshold excitation frequency divided by the square root of two.

Several benefits and advantages are derived from the invention which may be retrofitted to existing MRI scanners or designed into new MRI scanners. Locating the MRI gradient coil assembly in a vacuum reduces sound transmission. Locating the MRI gradient coil assembly in a higher pressure vacuum which is separate from the lower pressure vacuum of the superconductive main coil reduces cost. Using an isolation mount to support the MRI gradient coil assembly reduces the transmission of gradient coil assembly noise through the gradient coil assembly supports.

BRIEF DESCRIPTION OF THE DRAWINGS

The accompanying drawings illustrate a preferred enablement of the present invention wherein.

DETAILED DESCRIPTION OF THE INVENTION

Figure 1:
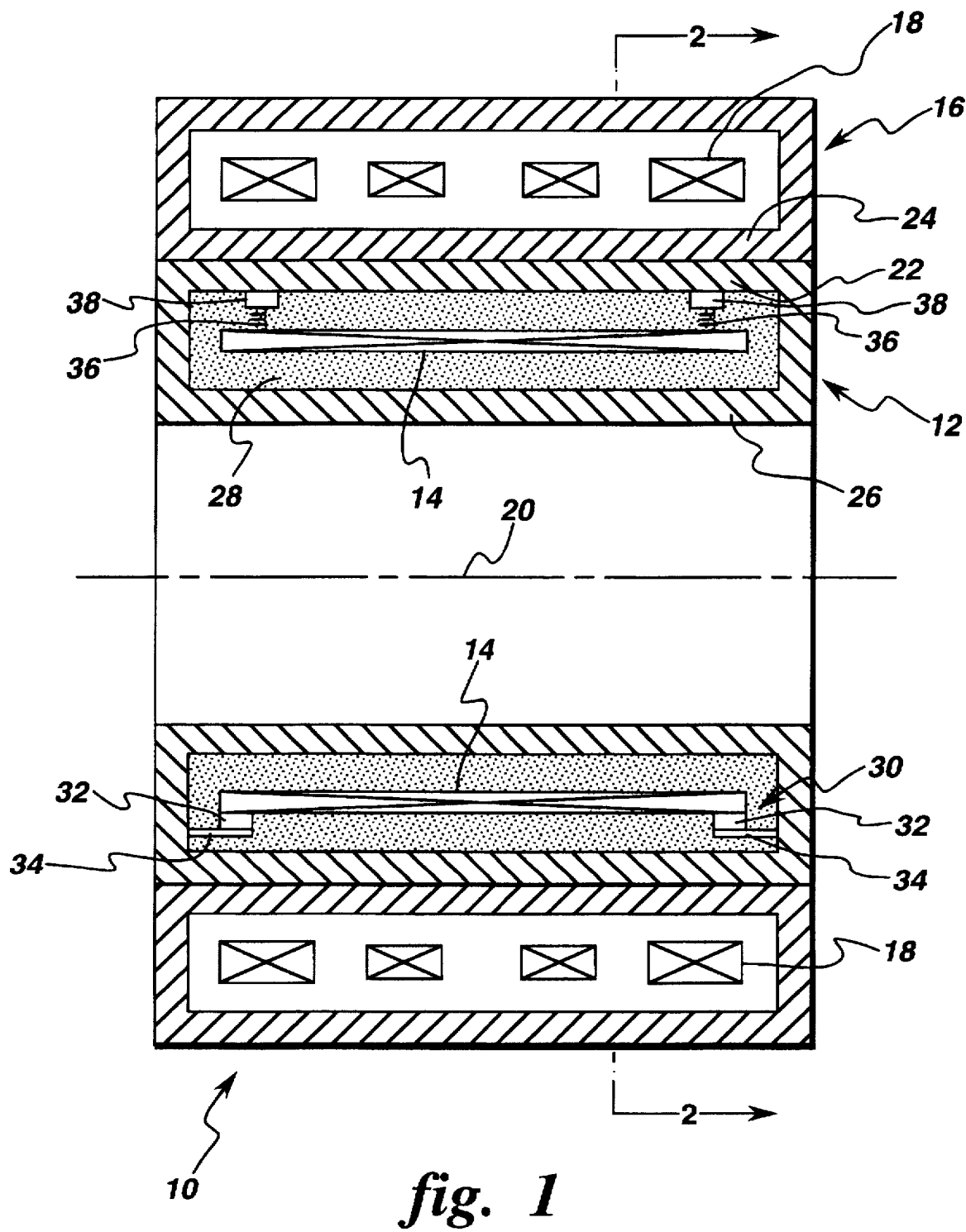
FIG. 1 is a schematic cross-sectional side-elevational view of an MRI scanner subassembly.
Figure 2:
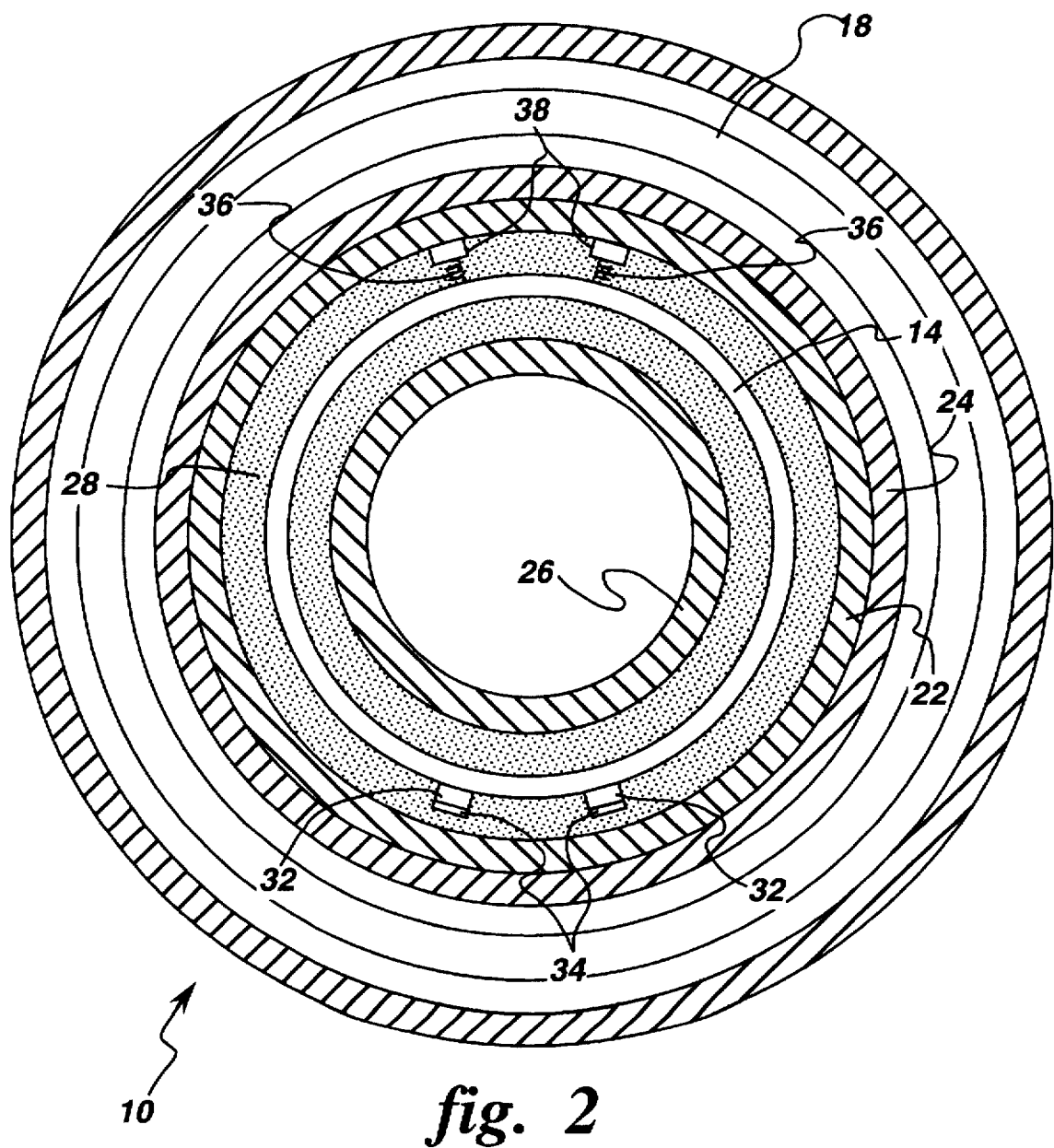
FIG. 2 is a schematic cross-sectional view of the MRI scanner subassembly of FIG. 1 taken along the lines 2—2 of FIG. 1.

Referring now to the drawings, wherein like numerals represent like elements throughout, FIGS. 1-2 show a preferred enablement of the magnetic-resonance-imaging (MRI) scanner subassembly 10 of the present invention. In a first preferred description of the invention, the MRI scanner subassembly 10 includes an enclosure 12 containing a first vacuum of between generally 1 and generally 250 torr. It is noted again that standard atmospheric pressure is defined to be 760 torr, that a vacuum is defined to have a pressure lower than that of atmospheric pressure. The MRI scanner subassembly 10 also includes an MRI gradient coil assembly 14 disposed within the enclosure 12 in the first vacuum and generally spaced apart from the enclosure 12. The MRI gradient coil assembly 14 typically comprises three gradient coils (not shown) having mutually orthogonal magnetic field directions. In this first preferred description of the present invention, the MRI gradient coil assembly 14 may be generally spaced apart from and supported by the enclosure 12 through any means and the MRI scanner may include any type of magnet to create the homogeneous magnetic field within the imaging volume, as can be appreciated by those skilled in the art. For example, and without limitation, the MRI scanner may have a closed or open magnet design and include a permanent magnet, a resistive-coil magnet, or a superconductive-coil magnet. It is noted that each magnetic assembly of an open magnet design would be associated with its own enclosure and its own MRI gradient coil assembly, as can be understood by those skilled in the art. It is further noted that a resistive-coil magnet or a permanent magnet preferably is exposed to ambient atmospheric pressure (generally 760 torr) and may even lack a housing.

In a second preferred description of the invention, the MRI scanner subassembly 10 includes an enclosure 12, an MRI gradient coil assembly 14, a housing 16, and an MRI superconductive main coil 18. The enclosure 12 is a generally annularly-cylindrical-shaped enclosure 12 having a generally longitudinally-extending axis 20 and containing a first vacuum. The MRI gradient coil assembly 14 is disposed within the enclosure 12 in the first vacuum and is generally spaced apart from the enclosure 12. The housing 16 is a generally annularly-cylindrical-shaped housing 16 generally coaxially aligned with the axis 20 and containing a second vacuum which is a lower pressure vacuum than the first vacuum. The MRI superconductive main coil 18 is generally aligned with the axis 20 and is disposed within the housing 16 in the second vacuum. The MRI superconductive main coil 18 is supported by the housing 16, such conventional coil-form and spacer supports, as well as any necessary thermal shield(s), liquid-helium dewars, cryocooler coldheads, and the like, being omitted from the figures for clarity. It is noted that the superconductive-coil magnet of an MRI scanner is made up of one or more superconductive main coils 18 (four of which are shown in FIG. 1) which generates a static magnetic field.

The MRI superconductive main coil 18 radially surrounds the MRI gradient coil assembly 14, and the housing 16 radially surrounds the enclosure 12. Preferably, the circumferentially-outer wall 22 of the enclosure 12 and the circumferentially-inner wall 24 of the housing 16 are generally abutting walls (as shown) or even the same wall (not shown). It is noted that an MRI scanner would also include an MRI radio-frequency (RF) coil assemblage (not shown) which typically is a single coil or includes two subcoils, which is radially surrounded by the MRI gradient coil assembly 14, and which (although not shown in the figures) preferably defines the circumferentially-inner wall 26 of the enclosure 12.

Preferably, the second vacuum is between generally $10^{-7}$ and generally $10^{-3}$ torr, and, preferably the first vacuum is between generally 1 and generally 250 torr. In an exemplary enablement, the second vacuum is generally $10^{-6}$ torr. The first vacuum may be referred to as an acoustic vacuum which reduces sound from the MRI gradient coil assembly 14 that would otherwise be transmitted through the surrounding air. The preferred range for the first vacuum was chosen with a recognition that a pressure below a high-pressure limit was needed to begin achieving a sound reduction benefit for the MRI patient and that a pressure below a low-pressure limit offered no added sound reduction benefit because of the sound from the MRI gradient coil assembly 14 that would be transmitted through its supports. A vacuum of 250 torr would result in a gradient coil assembly noise generally half as loud compared to atmospheric pressure. The second vacuum may be referred to as a magnet vacuum whose range is chosen for heat insulation reasons, as is within the skill of the artisan, to prevent the MRI superconductive main coil 18 from quenching. In a preferred construction, the MRI scanner subassembly 10 further includes sound-absorption material 28 disposed within the enclosure 12 generally surrounding (i.e., generally surrounding all surfaces of) the MRI gradient coil assembly 14 to further attenuate any residual sound in the first vacuum. A preferred sound-absorption material 28 is loose fiberglass insulation.

In this second preferred description of the present invention, the MRI gradient coil assembly 14 may be generally spaced apart from and supported by the enclosure 12 through any means, as can be appreciated by those skilled in the art, and the MRI scanner may have, for example and without limitation, a closed or open magnet design. It is noted that each magnetic assembly of an open magnet design would be associated with its own enclosure and its own MRI gradient coil assembly, as can be understood by those skilled in the art.

Locating the MRI gradient coil assembly in a moderate vacuum, separate from the lower pressure vacuum volume containing the main magnet windings, minimizes cost and maximizes performance by allowing the use in the gradient coil assembly, to support the coil wire, of inexpensive materials (e.g., rubber, plastic, epoxy) which have good acoustical properties but high vapor pressure. If these materials were located in the main magnet windings volume, their high vapor pressure might make it impossible to achieve the low pressure vacuum needed by the main magnet windings. Although these materials have significant vapor pressure at room temperature, it should be possible to pump down their vacuum space to, for example, 1 torr.

In a third preferred description of the invention, the MRI scanner subassembly 10 includes an MRI gradient coil assembly 14 excited by a predetermined series of multi-frequency electrical pulses having an electrical power, wherein generally five percent of said electrical power of said series comes from frequencies no higher than a threshold excitation frequency and generally ninety-five percent of said electrical power of said series comes from frequencies higher than said threshold excitation frequency. A typical threshold excitation frequency for an MRI gradient coil assembly 14 is in the range of generally 70 to generally 2,000 hertz. The MRI scanner subassembly 10 also includes an isolation mount assemblage 30 supporting the gradient coil assembly 14, wherein the isolation mount assemblage 30 and the MRI gradient coil assembly 14 together have a natural frequency of vibration which is less than the threshold excitation frequency of the MRI gradient coil assembly 14 divided by the square root of two. Such natural frequency of vibration can be so designed by adjusting the mass, stiffness, and damping of the isolation mount assemblage 30, as is within the knowledge and skill of the artisan. Preferably, the natural frequency of vibration is designed to be between generally 20 percent and generally 70 percent of the threshold excitation frequency. It is noted that a natural frequency of vibration that is close to the threshold frequency will result in an isolation mount assemblage 30 that will not do a good job of filtering out the vibration from the MRI gradient coil assembly 14, while a natural frequency of vibration that is too low (i.e., small) will result in an isolation mount assemblage 30 that will not be able to adequately support the MRI gradient coil assembly 14.

Preferably, the isolation mount assemblage 30 comprises a plurality of spaced-apart elastomeric isolation mounts 32. In a preferred construction, each of a multiplicity of rigid supports 34 is affixed to, or is a part of, the enclosure 12 and supports a corresponding one of the elastomeric isolation mounts 32. The isolation mount assemblage 30 of FIGS. 1 and 2 also includes spaced-apart spring isolation mounts 36 each having one of its two ends attached to the MRI gradient coil assembly 14 and each having the other of its two ends attached to an associated support flange 38 which is rigidly attached to, or is a part of, the inner surface of the circumferentially-outer wall 22 of the enclosure 12.

In this third preferred description of the present invention, the MRI scanner may include any type of magnet to create the homogeneous magnetic field within the imaging volume, as can be appreciated by those skilled in the art. For example, and without limitation, the MRI scanner may have a closed or open magnet design and include a permanent magnet, a resistive-coil magnet, or a superconductive-coil magnet. It is noted that each magnetic assembly of an open magnet design would be associated with its own enclosure and its own MRI gradient coil assembly as can be understood by those skilled in the art. It is further noted that a resistive-coil magnet or a permanent magnet preferably is exposed to ambient atmospheric pressure (generally 760 torr) and may even lack a housing.

For particular applications, the features of the first and second, or the first and third, preferred descriptions of the present invention may be combined. The MRI scanner subassembly 10 having such combined features would lower MRI gradient coil assembly 14 noise by utilizing the first vacuum in the enclosure 12 to reduce air-conducted sound transmission from the MRI gradient coil assembly 14 and by utilizing the isolation mount assemblage 30 to reduce solid-conducted sound transmission from the MRI gradient coil assembly 14. Here, it is noted, the MRI gradient coil assembly 14 and the isolation mount assemblage 30 are disposed within the enclosure 12 in the first vacuum, and the isolation mount assemblage 30 is supported by the enclosure 12 through the rigid supports 34 and the support flanges 38.

The foregoing several preferred descriptions of the invention have been presented for purposes of illustration. It is not intended to be exhaustive or to limit the invention to the precise form disclosed, and obviously many modifications and variations are possible in light of the above teaching. It is intended that the scope of the invention be defined by the claims appended hereto.

We claim:

1. A magnetic-resonance-imaging (MRI) scanner subassembly comprising:

a) a generally annularly-cylindrical-shaped enclosure having a generally longitudinally-extending axis and containing a first vacuum of between generally 1 and generally 250 torr;

b) an MRI gradient coil assembly disposed within said enclosure in said first vacuum and generally spaced apart from said enclosure, wherein said MRI gradient coil assembly is excited by a predetermined series of multi-frequency electrical pulses having an electrical power, and wherein generally five percent of said electrical power of said series comes from frequencies no higher than a threshold excitation frequency and generally ninety-five percent of said electrical power of said series comes from frequencies higher than said threshold excitation frequency;

c) a generally annularly-cylindrical-shaped housing generally coaxially aligned with said axis and containing a second vacuum which is a lower pressure vacuum than said first vacuum;

d) an MRI superconductive main coil generally coaxially aligned with said axis and disposed within said housing in said second vacuum; and e) an isolation mount assemblage supporting said MRI gradient coil assembly, wherein said isolation mount assemblage and said MRI gradient coil assembly together have a natural frequency of vibration which is less than said threshold excitation frequency divided by the square root of two.

2. The MRI scanner subassembly of claim 1, wherein said second vacuum is between generally $10^{-7}$ and generally $10^{-3}$ torr.

3. The MRI scanner subassembly of 1, also including sound-absorption material disposed within said enclosure generally surrounding said MRI gradient coil assembly.

4. The MRI scanner subassembly of claim 1, wherein said isolation mount assemblage comprises a plurality of spaced-apart elastomeric isolation mounts.

5. The MRI subassembly of claim 1, wherein said MRI gradient coil assembly comprises a material selected from the group consisting of rubber, plastic, and epoxy.

* * * * *